United States Patent [19]

Hasson

[11] Patent Number: 4,753,235
[45] Date of Patent: Jun. 28, 1988

[54] FORCEPS-TYPE SURGICAL INSTRUMENT

[76] Inventor: Harrith M. Hasson, P.O. Box 14898, Chicago, Ill. 60614

[21] Appl. No.: 911,147

[22] Filed: Sep. 24, 1986

[51] Int. Cl.$^4$ .............................................. A61B 17/00
[52] U.S. Cl. ................................... 128/321; 128/346; 128/354
[58] Field of Search ............... 128/303 R, 321, 346, 128/354

[56] References Cited

U.S. PATENT DOCUMENTS

| | | | |
|---|---|---|---|
| 1,974,106 | 9/1934 | Gardella | 128/354 |
| 2,042,985 | 6/1936 | Gardella | 128/354 |
| 2,049,520 | 8/1936 | Shaler | 128/354 |

Primary Examiner—C. Fred Rosenbaum
Assistant Examiner—Gene B. Kartchner
Attorney, Agent, or Firm—Wood, Dalton, Phillips, Mason & Rowe

[57] ABSTRACT

A forceps-type surgical instrument includes a tubular handle for grasping by a user and defining a longitudinal axis about which the handle can be rotated by a user's hand and fingers, the handle having an open distal end. A pair of forceps blades have proximal ends fixed within the tubular handle and distal ends projecting from the open end of the handle and terminating in functional jaws. The blades are spring biased toward a spread condition. An actuator member on the tubular handle is operative through the handle with at least one of the forceps blades for closing the blades in response to operating the actuator member by the user's finger.

18 Claims, 1 Drawing Sheet

U.S. Patent   Jun. 28, 1988   4,753,235
FIG. 1
PRIOR ART
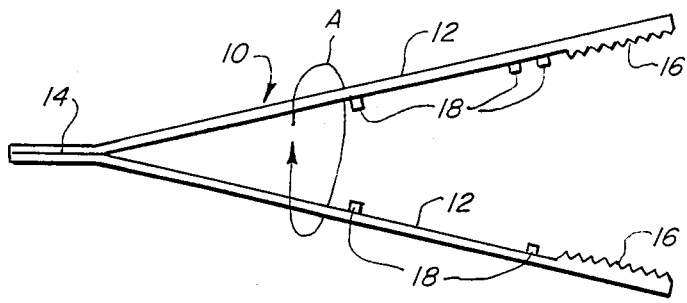
FIG. 2
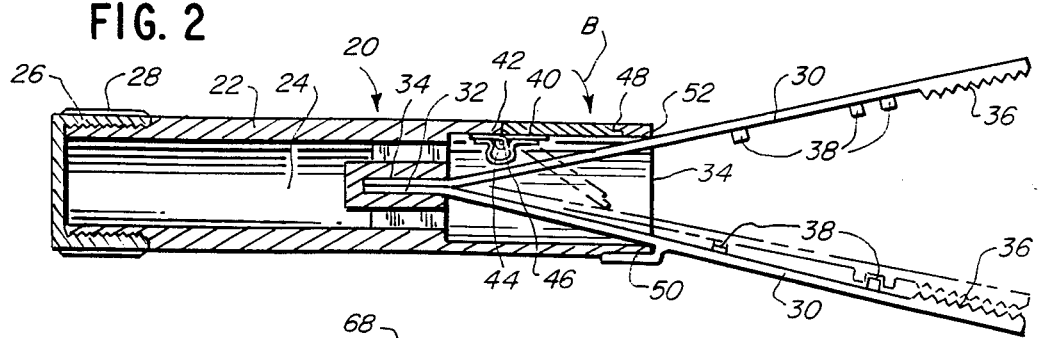
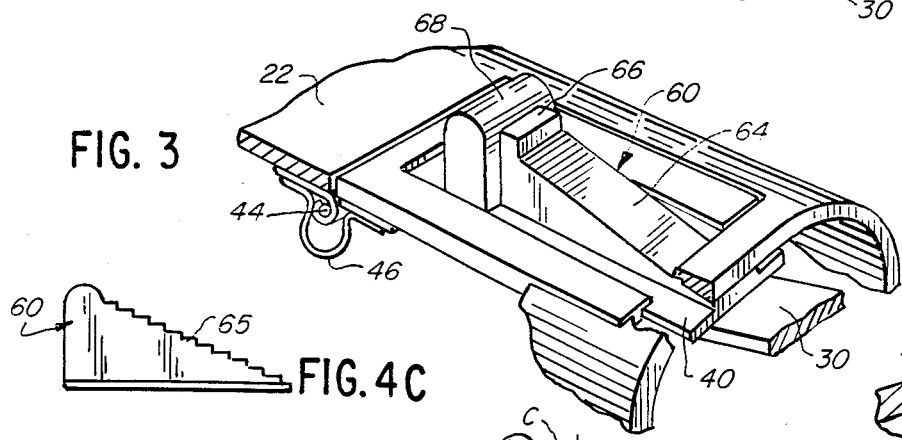
FIG. 3
FIG. 4C
FIG. 5
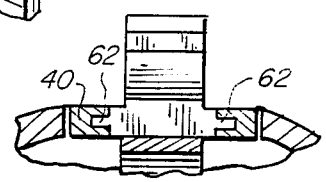
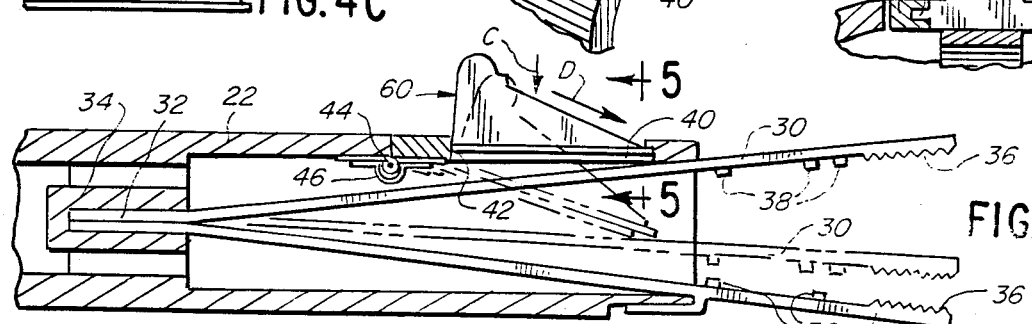
FIG. 4A
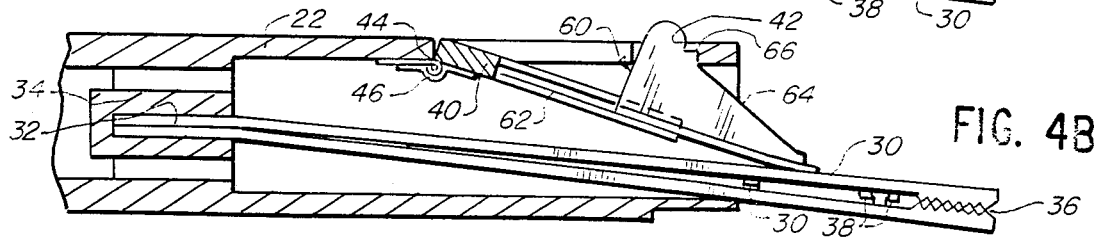
FIG. 4B

FORCEPS-TYPE SURGICAL INSTRUMENT

FIELD OF THE INVENTION

This invention generally relates to surgical or medical instruments of the forceps type conventionally used for grasping and manipulating body tissues or organs.

BACKGROUND OF THE INVENTION

Conventional forceps-type instruments of the character described normally include a pair of forceps blades which function in a tweezer-like action and are used in medical operations or surgery to hold, expose and manipulate tissues. Such instruments normally include two strips of metal in the form of blades joined at proximal ends and self-biased to an open condition at their distal ends in a V-shaped configuration. The distal ends of the blades comprise functional jaws which either are formed integral with the blades or built and mounted as inlays on the distal ends of the blades. Various restraining devices are formed on the medial sides of the blades to control closing pressure and/or prevent lateral sliding action of the blades and jaws. The jaws of the forceps come in different shapes and designs, including an open or closed ring, teeth, serrations, ridges or the like. The handle portions of the blades may be straight, angular or offset, or take the shape of a bayonet.

Such forceps-type surgical instruments are activated by a user, such as a surgeon, pressing on the spring-loaded blades to close the open distal ends and grasp tissues, needles or the like between the functional jaws. Conventional forceps instruments, such as the variety of instruments described above, are constructed such that activation of the forceps is limited to a single plane, i.e. the plane including the forceps blades. It is quite cumbersome to rotate such forceps, particularly flat-sided forceps, in the surgeon's hand or to close the forceps when rotated to various positions. In order to hold an area found along the natural arc of rotation of the forceps, it is necessary to rotate the entire hand at the surgeon's elbow by supination/pronation or at the wrist. Such movements are quite crude in comparison to movements created by the intrinsic muscles of the hand which are capable of great precision and finesse, particularly in the hands of a skilled surgeon. Furthermore, prolonged use of conventional forceps can result in fatigue and even tremors due to the unnatural movements required to rotate and manipulate forceps operable in a single plane.

This invention is directed to providing a forceps-type surgical instrument of the character described which may be easily held in the hand and manipulated by its intrinsic muscles and can be rotated comfortably and with precision by a surgeon's fingers.

SUMMARY OF THE INVENTION

An object, therefore, of the invention is to provide a new and improved surgical instrument of the forceps type which is easily held in the surgeon's hand, easily manipulated by its intrinsic muscles, held and/or rotated comfortably between the surgeon's fingers and activated to provide closing pressure with finer control for greater accuracy during delicate operations.

In the exemplary embodiment of the invention, the forceps-type surgical instrument includes a tubular handle for grasping by a user and defining a longitudinal axis about which the handle can be rotated by the user's hand and fingers. The handle has an open distal end. A pair of forceps blades have proximal ends fixed within the tubular handle and distal ends projecting from the open end of the handle and terminating in functional jaws. The blades are spring biased toward a spread condition. Actuator means are provided on the tubular handle and operatively associated therethrough with at least one of the forceps blades for closing the blades in response to operating the actuator means by the user's finger.

The proximal ends of the forceps blades are restrained and clamped within the tubular handle, and the forceps blades are spring-loaded so as to be biased apart toward their spread condition against opposite inner edges of the open end of the handle. In the preferred embodiment, one of the forceps blades is locked to the handle by complementary interengaging lip means between the one forceps blade and an edge of the open end of the handle, with the other forceps blade being positioned for closing against the one blade by the actuator means.

As disclosed herein, the actuator means comprises a spring-loaded door pivotally mounted in an opening in the handle for depressing by a user's finger to effect closing the forceps blades.

In an alternate form of the invention, means are provided on the pivotally mounted door for holding the door in various positions defining various degrees of closing the forceps blade, and also including a latch to define a partial or fully closed condition of the blades. In the exemplary embodiment of the invention, this means include a slide member on the spring-loaded, pivotally mounted door for sliding movement relative to the door into abutment with a lip on the underside of the handle at the open distal end thereof. The slide member includes a cam ramp for defining various degrees of closing the forceps blades and a latching ledge at the top of the cam ramp for locking the door in a position defining the fully closed condition of the forceps blades. Serrations may be provided on the cam ramp to latch the forceps in a preset degree of opening of the blades.

Other objects, features and advantages of the invention will be apparent from the following detailed description taken in connection with the accompanying drawings.

DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

FIG. 1 is an elevational view of a conventional blade-type forceps of the prior art;

FIG. 2 is a longitudinal or axial section, through the tubular handle, of the forceps-type surgical instrument of the invention;

FIG. 3 is a fragmented perspective view, on an enlarged scale, of the components of an alternate form of actuator means, including the slide member on the actuator door;

FIG. 4A is a fragmented axial section of the distal end of the instrument, incorporating the slide member of FIG. 3, with the forceps blades shown in full lines in fully open condition and in phantom in partially closed and latched condition;

FIG. 4B is a view similar to that of FIG. 4A, showing the slide member fully extended and locked to hold the forceps blades in fully closed condition;

FIG. 4C is an axial section of the cam ramp having serrations along the cam surface for latching the cam ramp in a selected position; and FIG. 5 is a fragmented section taken generally along line 5—5 of FIG. 4A.

DETAILED DESCRIPTION OF THE PREFERRED EMBODIMENTS

Referring to the drawings in great detail, and first to FIG. 1, a conventional tissue forceps, generally designated 10, is illustrated and includes a pair of flat forceps blades 12 fixed together at their proximal ends by angularly offset portions, as at 14. The blades conventionally are fabricated of metal material and are self-spring-biased toward a spread or open condition, as shown. The distal ends of blades 14 may include integral or inlaid functional jaws 16 for grasping tissues, body organs or the like therebetween. Restraining devices in the form of bosses 18 conventionally are provided on the inside faces of the forceps blades to control closing pressure. The restraining devices may include pin and aperture arrangements to prevent lateral shifting of the forceps blades relative to each other when in closed condition.

It can be understood from the visual depiction of prior art forceps instruments as described in relation to FIG. 1, that the forceps blades are activated in a single plane, i.e. the plane of the drawings. In order to rotate the instrument, as indicated by arrow "A", it is extremely cumbersome to effect such manipulation and requires a surgeon to rotate his entire hand at the elbow by supination/pronation or at the wrist. During prolonged operations, this oftentimes causes fatigue and even tremors because of the unnatural motions required by the arm, elbow and wrist. This invention, as described below, is designed to overcome these problems by providing a new and improved forceps-type surgical instrument which is extremely simple to hold, rotate and otherwise manipulate by using one's hand and its intrinsic muscles or by comfortable manipulation between the surgeon's fingers. For purposes of simplification, the term "finger" or "fingers" will be used herein and in the claims hereof and are intended to include the thumb as well as the fingers of the hand.

FIG. 2 shows one form of the forceps-type surgical instrument of this invention, generally designated 20. The instrument includes a tubular handle 22 which preferably is cylindrical in configuration for grasping by a surgeon and defining a longitudinal axis 24 about which the handle can be rotated by the surgeon's hand and/or fingers. A removable cap 26 is threaded onto the proximal end of handle 22, as at 28, to permit access to the interior of the handle for cleaning or repairs.

A pair of forceps blades 30 have proximal ends 32 fixed within tubular handle 22 by a press-fit with a fixed clamping boss 34. The distal ends of forceps blades 30 project from an open end 34 of handle 22 and terminate in functional jaws 36. The blades are fabricated of rigid, stiff material, such as metal, so as to be self-spring-biased outwardly toward a spread or open condition, as shown in FIG. 2. Restraining means 38 are provided on opposing inside faces of forceps blades 30 to control closing pressure and/or lateral shifting.

Generally, actuator means are provided on tubular handle 20, operatively associated therethrough with one of the forceps blades, for closing the blades in response to operating the actuator means by the surgeon's finger while still holding the handle. More particularly, an actuator member in the form of a trap-like door 40 is pivotally mounted in an opening 42 by a pivot hinge 44. The door is biased by a spring 46 in a direction to close opening 42. The forward edge of door 40 is undercut, as at 48, for mating with a similar undercut at the forward edge of opening 42 in the handle to provide a stop against which spring 46 holds the door in the condition shown in full lines in FIG. 2.

In order to further stabilize forceps blades 30, the lower blade, as viewed in FIG. 2, is locked to the front edge of open end 34 of handle 22 by means of a locking lip 50. In this manner, the lower blade is held stationary while the upper blade remains biased toward the opposite edge of the open end of the handle, as at 52.

In operation of the instrument illustrated in FIG. 2, handle 22 is held by the surgeon's hand and/or fingers and rotated comfortably between the thumb and the index and/or middle finger. The forceps thereby can be easily rotated or otherwise manipulated by natural movements with great precision and finesse utilizing the intrinsic muscles of the surgeon's hand, without requiring rotation of the surgeon's arm, elbow or wrist. When it is desired to close forceps blades 30 to grasp tissues, door 40 simply is depressed in the direction of arrow "B" whereby the door engages the top forceps blade (as viewed in the drawings) and biases the forceps blades together as shown in phantom in FIG. 2. Depression of the actuator means, defined by door 40, can be accomplished by the surgeon's thumb or even one of his fingers.

It can be understood that the ease of manipulation and rotation of instrument 20 is accomplished in a much wider arc of rotation than with conventional forceps instruments with straight configurations. The forceps blades can be easily closed at any point along the instrument's natural arc of rotation. Furthermore, once tissues or the like are held within the jaws of the forceps, it is possible to twist and/or rotate the held object gently without difficulty. On the other hand, such ease of motion and function is extremely difficult to accomplish with conventional tissue forceps as described in relation to FIG. 1. The instrument of this invention can be held and manipulated for long periods of time without fatigue or tremors by virtue of its ease of rotation and other manipulations, and the instrument can be activated to provide closing pressure with finer control for greater accuracy during delicate operations.

FIGS. 3-5 show an alternate form of the invention wherein, generally, means are provided operatively associated between door 40 and handle 22 for holding the door in various positions defining various degrees of closing forceps blades 30, as well as locking the forceps blades in fully closed condition. For simplification purposes, like numerals have been applied to FIGS. 4-5 to designate like components described above in relation to FIG. 2.

More particularly, a slide member, generally designated 60, is slidably mounted on the top of door 40 by means of a tongue-and-groove means 62 shown best in FIG. 5. An inclined cam ramp 64 is formed on the top of slide member 60, the cam ramp terminating at its upper end in a latching ledge 66. An enlarged push-button portion 68 is formed at the rear end of slide member 60.

In its inoperative condition as shown in full lines in FIG. 4A, slide member 60 is fully retracted rearwardly whereby door 40 is spring biased to a closed position, with forceps blades 30 fully opened. In order to close the forceps blades to a particular degree of closing movement, door 40 is depressed (similar to the action described in relation to FIG. 2) by pushing down on slide member 60 in the direction of arrow "C" (FIG. 4A). Once the front end of the door and slide member clear the front edge of opening 42 in handle 22, slide member 60 can be moved forwardly in the direction of arrow "D". This is shown in phantom in FIG. 4A. It can be seen that inclined cam ramp 64 defines practically an infinite number of stable closing positions for forceps blades 30.

FIG. 4B shows slide member 60 moved completely forwardly to fully close forceps blades 30. At this point, latch ledge 66 snaps beneath the undercut at the forward edge of opening 42 in handle 22 and is held in this locked position by the same spring 46 which biases door 40 toward closed condition. Movement of slide member 60 opposite the direction of arrow "D" (FIG. 4A), and release of the slide member and door 40, allows forceps blades 30 to spring back toward their fully open condition as shown in full lines in FIG. 4A, or to any intermediate position depending upon how far back the slide member is moved.

Substituting the cam ramp 64 on slide member 60 of FIG. 4C with parallel serrations 65 extending across the surface of the ramp will permit the cam ramp to be latched in a preselected position with a selected serration 65 engaging the undercut at the forward edge of opening 42. In this way, upon release of the slide member 60 and door 40 will permit the slide member 60 and door 40 to open only to the extent allowed by one of the serrations 65 engaging the edge of the opening 42.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A forces-type surgical instrument comprising:
   a tubular handle for grasping by a user and defining a longitudinal axis by which the handle can be rotated by a user's hand and finges, the handle having an open distal end;
   a pair of forceps blades having proximal ends fixed within a tubular handle and distal ends projecting from the open end of the handle and terminating in functional jaws, the blades being spring biased toward a spread condition; and
   actuator means on the tubular handle and operatively associated therethrough with at least one of the forceps blades for closing the blades in response to operating the actuator means by the user's fingers, said actuator means including
   an actuator member pivotally mounted at its proximal end in an opening in the handle,
   means for biasing the actuator member away from said one forcep blade, and
   means for retaining the actuator member within the handle.

2. The instrument of claim 1, including means for clamping the proximal ends of the forceps blades within the tubular handle.

3. The instrument of claim 2, wherein the forceps blades are spring-loaded so as to be biased apart toward said spread condition against opposite inner edges of the open end of the handle.

4. The instrument of claim 1, including means for locking one of the forceps blades to the handle, with the other forceps blade being positioned for closing against the one blade by said actuator means, said locking means comprising complementary interengaging lip means between the one forceps blade and an edge of the open end of the handle.

5. The instrument of claim 1, including means operatively associated between said actuator member and the handle for holding the actuator member in various positions defining various degrees of closing of the forceps blades.

6. The instrument of claim 1, wherein said actuator member comprises a door, said door including a slide member pivotally mounted in an opening in the handle for depressing by a user's finger to effect closing the forceps blades, and operatively associated with the handle for holding the door in various position defining various degrees of closing the forceps blades.

7. The instrument of claim 6, including complementary latch means between said slide member and the handle for locking the door in a position defining a fully closed condition of the forceps blades.

8. A forceps-type surgical instrument comprising:
   a tubular handle for grasping by a user and defining a longitudinal axis about which the handle can be rotated by a user's hand and fingers, the handle having an open distal end;
   a pair of forceps blades having proximal ends fixed within a tubular handle and distal ends projecting from the open end of the handle and termianting in functional jaws, the blades being spring biased toward a spread condition; and
   actuator means on the tubular handle and operatively associated therethrough with at least one of the forceps blades for closing the blades in response to operating the actuator means by the user's fingers, said actuator means including
   a door pivotally mounted in an opening in the handle for depressing by a user's finger to effect closing a forceps blades, and
   a slide member on said door and operatively associated with the handle for holding the door in various positions defining various degrees of closing the forceps blades, said slide member having an inclined cam ramp engageable with an edge of the opening in the handle to define the various degrees of closing the forceps blades.

9. The instrument of claim 8, including a latch ledge at the top of said inclined cam ramp for locking the door in a position defining a fully closed condition of the forceps blades.

10. A forceps-type surgical instrument, comprising:
    a tubular handle for grasping by a user and defining a longitudinal axis about which the handle can be rotated by a user's hand and fingers, the handle having an open distal end;
    a pair of forceps blades having proximal ends fixed within the tubular handle and distal ends projecting from the open end of the handle and terminating in functional jaws, the blades being spring biased toward a spread condition;

a spring-loaded door pivotally mounted in an opening in the handle for depressing by a user's finger to engage one of the forceps blades to effect closing the forceps blades;

a slide member on said door operatively associated with the handle for holding the door in various positions defining various degrees of closing the forceps blades; and complementary latch means between said slide member and the handle for locking the door in a position defining a fully closed condition of the forceps blades.

11. The instrument of claim 10, including means for clamping the distal ends of the forceps blades within the tubular handle.

12. The instrument of claim 11, wherein the forceps blades are spring-loaded so as to be biased apart toward said spread condition against opposite inner edges of the open end of the handle.

13. The instrument of claim 10, including means for locking the other of said forceps blades to the handle, with said one forceps blade being engageable by said door, said locking means comprising complementary interengaging lip means between the other forceps blade and an edge of the open end of the handle.

14. A forceps-type surgical instrument, comprising:

a cylindrical handle for grasping by a user and defining a longitudinal axis about which the handle can be rotated by the user's hand and fingers, the handle having an open distal end;

a pair of forceps blades having proximal ends fixed within the tubular handle and distal ends projecting from the open end of the handle and terminating in functional jaws, the blades being spring biased toward a spread condition; and actuator means on the cylindrical handle and operatively associated with at least one of the forceps blades for closing the blades in response to operating the actuator means, said actuator means including an actuator member pivotally mounted at its proximal end in an opening in the handle, means for biasing the actuator member away from said one forceps blade, and means for retaining the actuator member within the handle.

15. The instrument of claim 14, including means operatively associated between said actuator member and the handle for holding the actuator member in various positions defining various degrees of closing of the forceps blades.

16. The instrument of claim 14, wherein said actuator member comprises a spring-loaded door pivotally mounted in an opening in the handle for depressing by a user's finger to effect closing the forceps blades, said spring-loaded door including a slide member, and operatively associated with the handle for holding the door in various positions defining various degrees of closing the forceps blades.

17. The instrument of claim 16, including complementary latch means between said slide member and the handle for locking the door in a position defining a fully closed condition of the forceps blades.

18. A forceps-type surgical instrument, comprising:

a cylindrical handle for grasping by a user and defining a longitudinal axis about which the handle can be rotated by a user's hand and fingers, the handle having an open distal end;

a pair of forceps blades having proximal ends fixed within a tubular handle and distal ends projecting from the open end of the handle and terminating in functional jaws, the blades being spring biased toward a spread condition;

actuator means on a cylindrical handle and operatively associated with at least one of the forceps blades for closing the blades in response to operating the actuator means, said actuator means including an actuator member comprising a door pivotally mounted in an opening in the handle for depressing by the user's finger to effect closing of the forceps blades, and a slide member on said door and operatively associated with the handle for holding a door in various positions defining various degrees of closing the forceps blades, said slide member having an inclined cam ramp engageable with an edge of the opening in the handle to define the various degrees of closing the forceps blades.

* * * * *